United States Patent [19]
Green

[11] 4,097,835
[45] Jun. 27, 1978

[54] DUAL TRANSDUCER ARRANGEMENT FOR ULTRASONIC IMAGING SYSTEM

[75] Inventor: Philip S. Green, Atherton, Calif.

[73] Assignee: SRI International, Menlo Park, Calif.

[21] Appl. No.: 724,416

[22] Filed: Sep. 20, 1976

[51] Int. Cl.² .............................................. G01S 9/66
[52] U.S. Cl. .................................... 340/1 R; 73/626; 73/628; 73/641; 73/642; 310/335; 310/369; 340/3 D; 340/8 L; 128/2.05 F; 128/2.05 Z
[58] Field of Search ................... 340/1 R, 3 D, 8 L; 73/67.8 R, 67.8 S, 194 A; 310/9.8, 9.6, 335, 336, 369; 128/2 V, 2.05 F, 2.05 V

[56] References Cited

U.S. PATENT DOCUMENTS

| 2,549,872 | 4/1951 | Willard | 340/8 L |
|---|---|---|---|
| 3,090,030 | 5/1963 | Schuck | 340/1 R |
| 3,233,450 | 2/1966 | Fry | 73/67.8 S |
| 3,430,625 | 3/1969 | McLeod, Jr. | 340/3 D |

*Primary Examiner*—Richard A. Farley
*Attorney, Agent, or Firm*—Victor R. Beckman

[57] ABSTRACT

Combination Doppler and B-scan ultrasonic imaging apparatus is disclosed which includes visual display means for the simultaneous visual display of received ultrasonic Doppler and B-scan information. The apparatus includes first and second focused transducers associated with the Doppler and B-scan systems, which transducers are individually mounted for movement along parallel linear paths. The transducers each comprise a generally semi-cylindrical shaped body of piezoelectric material having opposite end faces upon which electrodes are disposed for connection to Doppler and B-scan transmitter and/or receiver units. The flat side walls of the piezoelectric bodies are positioned closely adjacent a mid-plane extending between the transducers, and means are provided for focusing the transducers at substantially the same depth for operation along a common focal region at, or adjacent, the mid-plane. One such focusing means includes acoustic lenses carried by the piezoelectric bodies. Another focusing means includes an electrode array for connection to the transmitter and/or receiver units through signal delay means. In yet another embodiment, the piezoelectric bodies are formed with curved end faces for focusing.

18 Claims, 7 Drawing Figures

DUAL TRANSDUCER ARRANGEMENT FOR ULTRASONIC IMAGING SYSTEM

ORIGIN OF INVENTION

The invention described herein was made in the course of a contract with the Department of Health, Education and Welfare.

BACKGROUND OF THE INVENTION

This invention relates to a dual ultrasonic motion detecting and imaging system used, for example, to provide a simultaneous display of Doppler information signals and a B-scan image. More particularly, the invention is directed to an arrangement comprising first and second transducers which are movable along parallel linear paths which are closely spaced for minimizing the angle between the acoustic axes of the transducers when the transducers are located directly opposite one another.

Ultrasonic imaging systems capable of providing a combined B-scan and Doppler display are well known as shown, for example, in an article in IEEE TRANSACTIONS ON BIOMEDICAL ENGINEERING, Vol. 1 BME-21, No. 2, March 1974 entitled, "Ultrasonic Duplex Echo-Doppler Scanner" by Frank E. Barber et al. Similarly, a combined B-scan and Doppler display is suggested in a report entitled, "Development of High Resolution Ultrasonic Imaging Techniques for Detection and Clinical Assessment of Cardiovascular Disease" dated 9/5/74 by Titus C. Evans, Philip S. Green, and James F. Greenleaf, Report No. N01-HT-4-2904-1 available from the National Technical Information Service, 5285 Port Royal Road, Springfield, Virginia, 22151.

Where a simultaneous display of B-scan and Doppler information at a single display is provided, it is desirable that the Doppler information for such display be obtained from within the B-scan section being imaged. Such desideratum may be achieved by use of a single transducer which is multiplexed for operation with both the Doppler and B-scan systems. Such multiplex operation of the transducer places severe restraints on the operating rates and frequencies for each system.

SUMMARY OF THE INVENTION AND OBJECTS

An object of this invention is the provision of an improved dual ultrasonic transducer system for use with a combined imaging and motion detecting and display system.

An object of this invention is the provision of an ultrasonic transducer system employing a pair of focused ultrasonic transducers movable along parallel linear paths, which transducers are of such a shape and design as to minimize the angle formed between the transducer acoustic axes when the transducers are positioned directly opposite one another in traveling along the movable paths.

The above and other objects and advantages are achieved by use of a pair of ultrasonic transducers, each of which comprises a piezoelectric body of generally semicylindrical shape having generally parallel semicircular opposite end faces and flat and semicylindrical side walls. Electrodes are disposed on the opposite end faces for connection to the desired ultrasonic transmitter and/or receiver units. The transducers are mounted with the flat side wall directly opposite a mid-plane extending between the transducers, and are adapted for movement along generally parallel linear paths for scanning the subject under investigation. Also, they are focused at, or adjacent, the midplane at substantially equal distances from the transducers. Focusing may be provided by use of acoustic lenses associated with the transducers, by proper curvature of the piezoelectric body members, by the use of an electrode array at at least one face of the piezoelectric bodies, or the like.

The invention, as well as the above objects and advantages thereof, will become apparent from the following detailed description when considered with the accompanying drawings.

BRIEF DESCRIPTION OF THE DRAWINGS

In the drawings, wherein like reference characters refer to the same parts in the several views.

Figure 1:
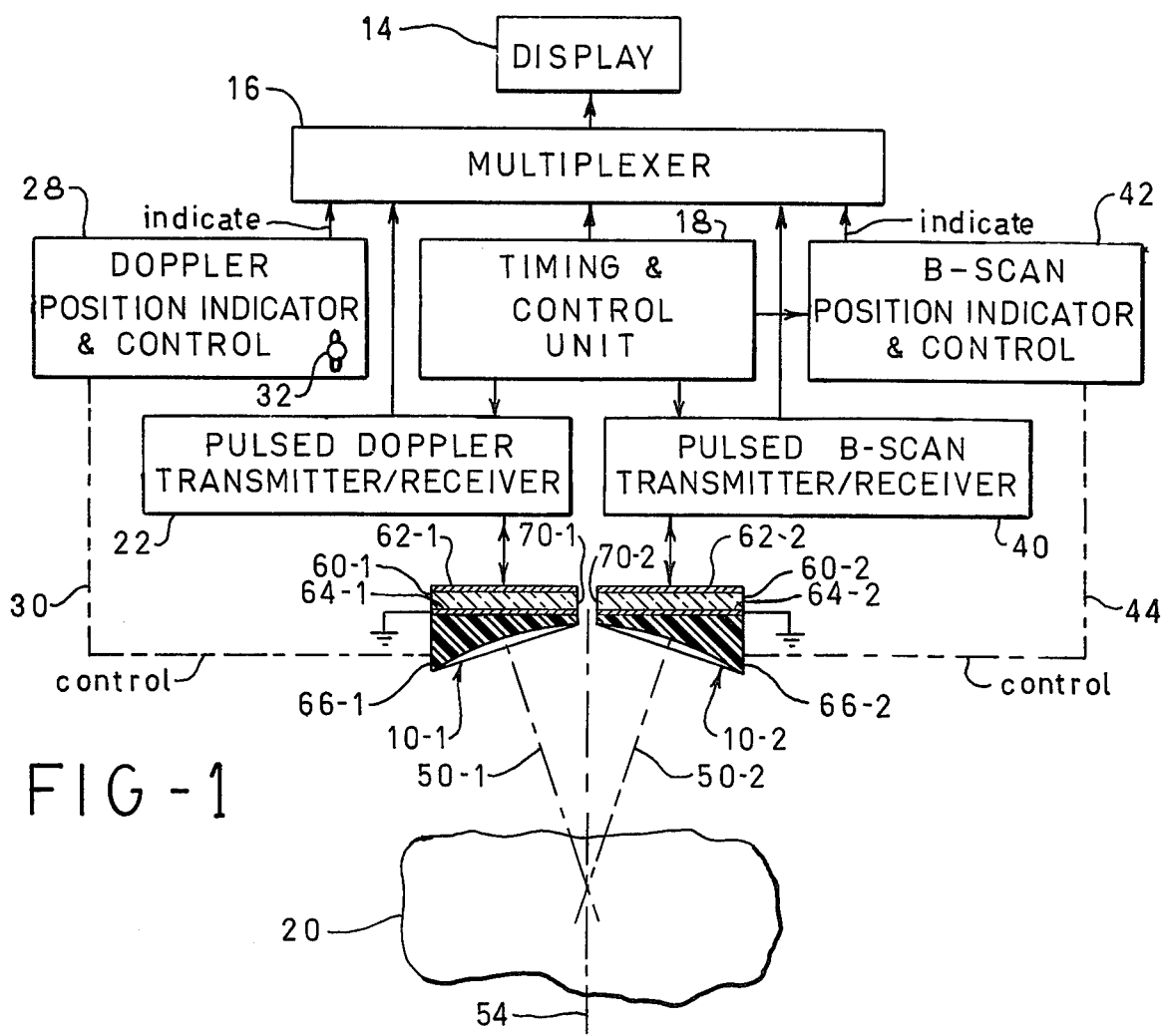
FIG. 1 is a combination block and diagrammatic view of a combination ultrasonic imaging and movement detecting system employing the novel transducer system of this invention.

Reference first is made to FIG. 1 wherein one embodiment of the dual transducer arrangement of this invention is shown comprising first and second ultrasonic transducers 10-1 and 10-2 which are employed in a movement sensing and imaging system. The ultrasonic movement detecting and imaging units associated with the novel dual transducer system of this invention may be of conventional design and, for purposes of illustration, are shown comprising pulsed ultrasonic Doppler blood flow sensing means and pulsed B-scan imaging means, respectively, having outputs which are displayed at a common display unit 14 through use of a multiplexer 16. Typically, the display unit may comprise a cathode ray tube to which Doppler and B-scan receiver signals are connected, and to which suitable deflector signals simultaneously are supplied for sweeping of the spot across the face of the cathode ray tube screen. The transducers 10-1 and 10-2 are located in a suitable acoustic transmission medium, such as water, (not shown) for the support of acoustic waves produced thereby and echo signals received from an object 20 suitably acoustically coupled to the liquid medium.

For purposes of illustration, the pulsed Doppler system is shown comprising a transmitter/receiver unit 22 for the recurrent generation of high frequency electrical energy pulses under control of timing and control unit 18, which pulses are supplied to the first transducer 10-1. The resultant focused ultrasonic waves from the transducer 10-1 are transmitted through a liquid medium, not shown, to the subject 20 for pulse insonification thereof at a first frequency. Echo signals from discontinuities within the subject 20 received by the transducer 10-1 are converted to electrical signals which are supplied to the receiver portion of the pulsed Doppler transmitter/receiver unit for signal processing. Doppler signals from moving discontinuities, such as blood cells, and detected by the receiver, are connected to the display unit 14 through the multiplexer 16 for display thereat.

Because separate transducers 10-1 and 10-2 are used for the Doppler and B-scan systems, the transducers may be designed for operation at widely different frequencies for the avoidance of acoustic interference between Doppler and B-scan signals. Consequently, the Doppler and B-scan systems may be asychronously operated. When operated asychronously, the receiver B-scan signals from the B-scan receiver, described below, may be immediately displayed to provide a real time B-scan image display, and the received Doppler signals may be displayed between selected B-scan display lines. For such operation, the Doppler receiver within unit 22 may include signal storage means for the temporary storage of Doppler signals received during B-scan display, and from which stored Doppler signals are read out to the display unit 14 through the multiplexer 16 during selected periods between the display of B-scan signals.

Figure 2:
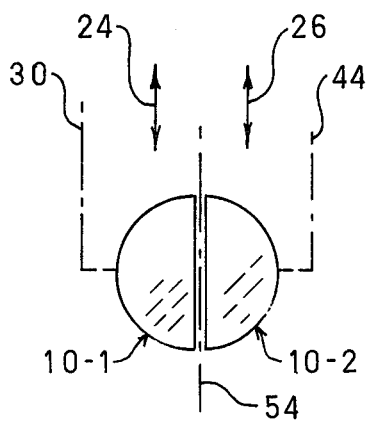
FIG. 2 is a sectional view, on a reduced scale, taken along line 2—2 of FIG. 1.
Figure 3:
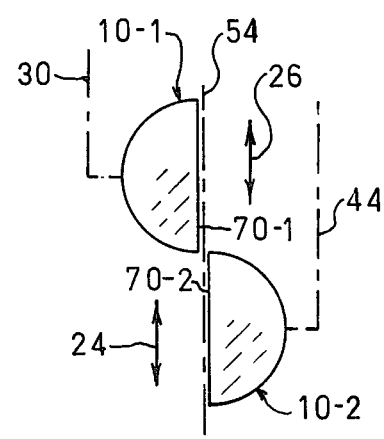
FIG. 3 is a view which is similar to that of FIG. 2 but showing the transducers longitudinally displaced along the scan paths.

The transducers 10-1 and 10-2 are movable along parallel linear paths in the directions of double-headed arrows 24 and 26, respectively, shown in FIGS. 2 and 3. The Doppler transducer 10-1 is positionable anywhere along its scan path under control of the Doppler Transducer Position and Control unit 28 connected thereto through mechanical control linkage 30. A servomotor may be included in the unit 28 for mechanical actuation of the transducer 10-1 under control of a lever 32 at the front panel of the control unit. In FIG. 2, the Doppler and B-scan transducers are shown positioned directly opposite one another, and in FIG. 3 they are shown at opposite ends of their respective scan paths. Electrical Doppler transducer position information is supplied to the display unit 14 through the multiplexer 16 from the control unit 28 to provide one deflection signal thereto for proper positioning of the Doppler display at the face of the display unit. An orthogonal deflection signal for Doppler display is supplied from the timing and control unit 18 through the multiplexer.

The pulsed B-scan system, for purposes of illustration, comprises a transmitter/receiver unit 40 for the recurrent generation of high frequency energy pulses which are supplied to the B-scan transducer 10-2. As noted above, different operating frequencies may be employed for the Doppler and B-scan systems to avoid interference between the acoustic energy waves. The focused ultrasonic wave pulses from the B-scan transducer 10-2 pass through the liquid medium, not shown, and into the subject 20 for pulse insonification thereof. Echo signals received by the transducer 10-2 from discontinuities within the region of the ultrasonic beam are converted to electrical signals which are supplied to the receiver section of the transmitter/receiver unit 40. The B-scan receiver is gated on after a delay period following generation of the last B-scan pulse for receiving echo signals from within a range of depths along the beam within the subject 20.

A B-scan Transducer Position Indicator and Control unit 42, connected to the B-scan transducer 10-2 through mechanical control linkage 44, serves to periodically sweep the transducer back and forth along its scan path, in the direction of arrow 26, to provide for a two-dimensional B-scan display. A deflection signal related to the B-scan transducer position along its path of travel is provided to the display unit through the multiplexer 16 from the position indicator portion of the B-scan Transducer Position Indicator and Control unit 42 for deflection of the spot at the display unit 14 in one direction. An orthogonal deflection voltage related to the time elapsed from the last transmitted B-scan pulse is supplied to the display unit from the Timing and Control Unit 18 for deflection of the spot in an orthogonal direction. The B-scan receiver output is connected as a Z-axis signal for the display unit for intensity modulation of the B-scan display in accordance with the amplitude of receiver output signals. A real-time display of the B-scan system thereby is provided, without storage of the B-scan signals.

From the above, it will be understood that a section within the object 20 which lies along the acoustic axis 50-2 of the B-scan transducer 10-2, and in a plane normal to the plane of the drawing of FIG. 1, is imaged by the B-scan system. The Doppler signal, on the other hand, is obtained from along the acoustic axis 50-1 of the Doppler transducer which intersects the imaged B-scan section. For ease in interpreting the visual display of the combined Doppler and B-scan signals at the display unit 14, the Doppler transducer axis should lie in the B-scan imaged section. Such ideal situation is not possible, however, where the Doppler and B-scan transducers are movable along parallel paths as in the illustrated arrangement. However, with the novel transducer system of this invention, now to be described, the Doppler and B-scan acoustic axis, at the transducer faces, may be closely positioned thereby minimizing the angle between the Doppler transducer axis and the B-scan image plane.

In accordance with the present invention the transducers 10-1 and 10-2 are formed of generally semicylindrical-shaped bodies 60-1 and 60-2, respectively, of piezoelectric material of any suitable type, such as barium titanate, or the like. The piezoelectric members are formed with generally parallel opposite end surfaces upon which electrodes 62-1 and 64-1 and electrodes 62-2 and 64-1 are disposed. The electrodes 62-1 and 62-2 are connected to the Doppler and B-scan transmitter/receiver units 22 and 40, respectively, whereas the electrodes 64-1 and 64-2 at the opposite faces thereof are connected to ground potential.

A variety of means for focusing the transducers are available and several such focusing means presently are illustrated. In the arrangement of FIGS. 1–3 lenses 66-1 and 66-2 are provided at the front faces of the transducer bodies for focusing. One face of each lens is of the same semicircular shape as the associated face of transducer body to which the lens is secured. The opposite lens faces are suitably concavely curved to provide the transducers with the desired focus. Any suitable means, such as cement, may be used to affix the lenses to the transducer bodies. Also, the lenses may be formed of any suitable material, such as polystyrene, which often is employed because of its low sound absorption characteristics. Obviously, other materials may be employed. Also, compound lenses employing a plurality of lens elements may be used. The acoustic lenses may employ liquid as well as solid materials as is well understood in the lens art. In the illustrated arrangement, solid lens elements of such shape and material to provide the transducers with the above-mentioned acoustic axes 50-1 and 50-2 for focusing at a common distance from the face of the transducer along the midplane 54 are employed.

With the novel transducer arrangement of this invention, the flat sides 70-1 and 70-2 of the generally semicylindrical-shaped transducers are positioned closely adjacent the mid-plane 54 and, as mentioned above, the transducers are movable along parallel linear paths in the direction of arrows 24 and 26. They are provided with the desired scanning movement along said paths under control of units 28 and 42 connected thereto through the mechanical linkages 30 and 44, respectively. By locating the flat sides of the transducers closely adjacent the mid-plane 54, the transducer axes 50-1 and 50-2 intersect the plane at a minimum angle for any given length focus. Consequently, the displacement of the Doppler display from the B-scan image is substantially less than if, for example, complete cylindrical-shaped piezoelectric bodies were employed. Of course, with the present arrangement, the lateral resolution of the transducers in the direction of scan is twice that of the resolution in the direction orthogonal to the scan.

Figure 4:
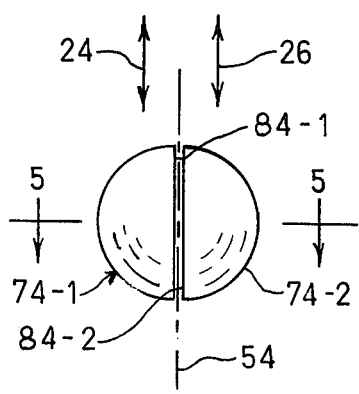
FIG. 4 is a plan view showing a modified form of this invention employing transducers having curved piezoelectric bodies for focusing.
Figure 5:
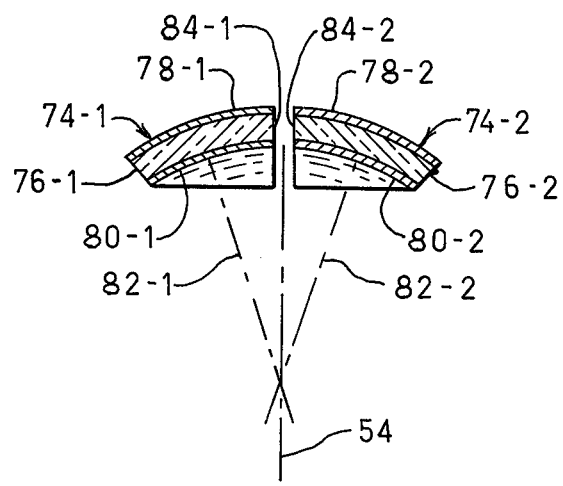
FIG. 5 is a sectional view, on an enlarged scale, taken along line 5—5 of FIG. 4.

Other means for focusing the transducers are contemplated. For example, in the embodiment illustrated in FIGS. 4 and 5, the piezoelectric transducer bodies are suitably curved to provide the necessary focusing. There, transducers 74-1 and 74-2, comprising generally semi-cylindrical-shaped bodies 76-1 and 76-2 of piezoelectric material with electrodes 78-1 and 80-1, and 78-2 and 80-2, at opposite body faces, are shown. The transducers 74-1 and 74-2 are of substantially the same design as those shown in FIGS. 1-3 and described above, except that the active faces thereof are generally concavely curved to provide the transducers with the desired focusing action. The acoustic axes 82-1 and 82-2 of the illustrated transducers intersect at the mid-plane 54. Also, the flat inner transducer edges 84-1 and 84-2 are closely spaced adjacent the mid-plane, and the transducers are movable along generally parallel linear paths in the direction of arrows 24 and 26, respectively. The transducers are adapted for use in the same combination Doppler/B-scan imaging system of the type disclosed in FIG. 1. Unlike the FIGS. 1-3 transducer system, the transducers 74-1 and 74-2 require no acoustic lenses for focusing.

Figure 6:
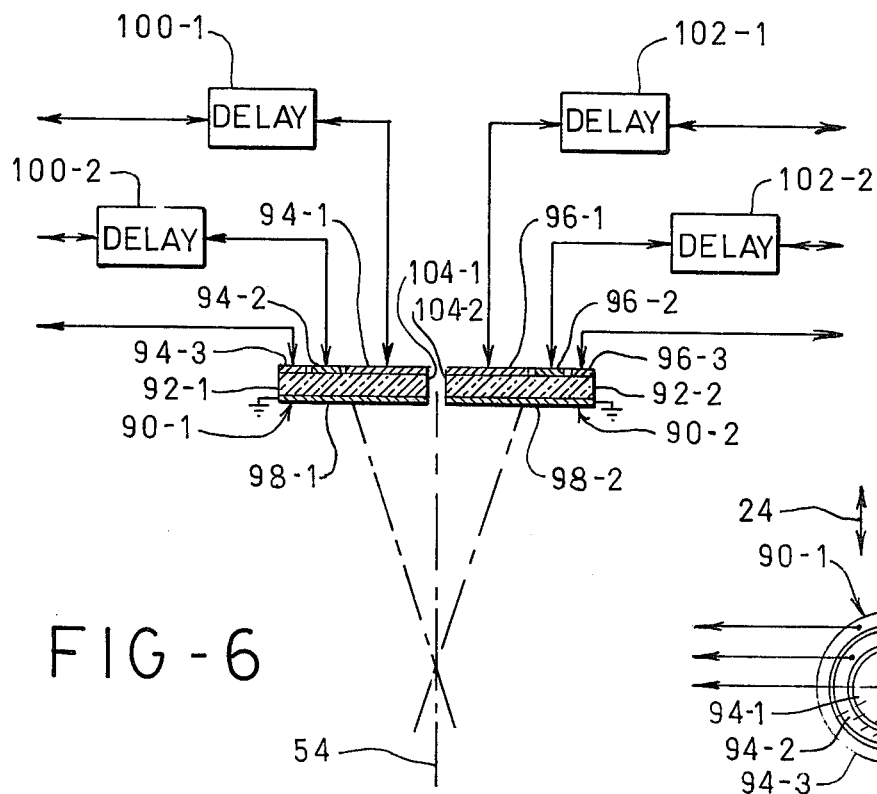
FIG. 6 is a cross-sectional view showing another modified form of transducer system employing electrode arrays at the piezoelectric bodies of the transducers for use in focusing.
Figure 7:
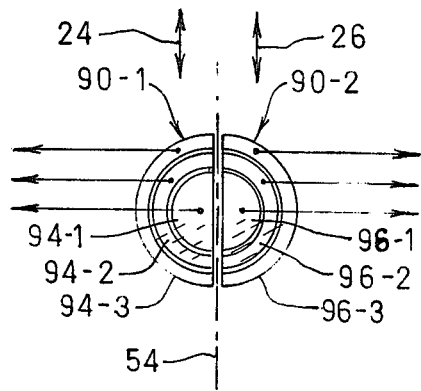
FIG. 7 is a top view of the transducer system shown in FIG. 6 and showing, on a reduced scale, the electrode array at the upper faces of the transducers.

In another modified form of the invention, shown in FIGS. 6 and 7, electronic focusing of the illustrated transducers 90-1 and 90-2 is provided. There, the transducers are shown comprising flat generally semicylindrical-shaped bodies, or plates, 92-1 and 92-2 of piezoelectric material which may be of the same shape as the piezoelectric bodies 60-1 and 60-2 employed in the FIGS. 1-3 arrangement. For the FIGS. 6 and 7 arrangement the piezoelectric plates are polarized normal to the opposite parallel faces thereof during manufacture as by exposure to a unidirectional electric field thereacross.

The upper faces of the piezoelectric plates 92-1 and 92-2, opposite the lower active transducer surfaces, thereof, are provided with a plurality of axially aligned electrodes 94-1, 94-2 and 94-3 and 96-1, 96-2 and 96-3, respectively. The central electrodes 94-1 and 96-1 are of semicircular shape, and the outer electrodes 94-2 and 94-3, and 96-2 and 96-3 are of semiannular shape. The above-described electrodes on the upper surfaces of the transducer bodies overlie counter electrodes 98-1 and 98-2 which cover the entire active lower surfaces thereof. Alternatively, the lower active transducer body surface may be provided with electrodes of the same dimensions as the electrodes 94-1, 2 and 3, and 96-1, 2 and 3, directly underlying the same. As is well understood, active transducer zones are provided within the piezoelectric plates as determined by the dimensions of the concentric electrodes disposed thereon. The electrodes 94-1, 2 and 3 are connected to pulsed Doppler transmitter/receiver, not shown, and the electrodes 96-1, 2 and 3 are connected to a pulsed B-scan transmitter/receiver, not shown in FIGS. 6 and 7. Delay lines 100-1 and 100-2, and 102-1 and 102-2, are included in the connection of the transducer electrodes 94-1 and 94-2, and 96-1 and 96-2 to the respective Doppler and B-scan transmitter units. Transmitter/receiver units of the type shown in FIG. 1 and described above may be employed in the FIGS. 6 and 7 arrangement.

The transducers 90-1 and 90-2 illustrated in FIGS. 6 and 7 comprise, essentially, opposite halves of a conventional zone plate type transducer of a well known type. Such prior art zone plate transducers are provided with a plurality of active transducer zones, generally numbering from, say, five to seven. For simplicity, only three zone plates are shown in the illustrated transducer arrangement. With the proper delays, the transducers may be operated to focus along a wide range of acoustic axes within the plane of drawing FIG. 6. Obviously, variable delay means may be used for operation of the transducers along different axes, and at different depths. As with the other transducer arrangements embodying this invention, the flat sides 104-1 and 104-2 of the transducers are closely spaced adjacent the midplane 54, and the transducers are movable along parallel linear paths in the direction of arrows 24 and 26, respectively.

The invention having been described in detail in accordance with the requirements of the Patent Statutes, various other changes and modifications will suggest themselves to those skilled in the art. For example, the transducers may be focused along generally parallel acoustic axes for operation along parallel focused regions at opposite sides of the mid-plane but relatively closely located adjacent thereto. It is intended that the above and other such changes and modifications shall fall within the scope and spirit of the invention as defined in the appended claims.

I claim:

1. In an ultrasonic imaging apparatus of the type which includes different operating systems, such as systems which operate in the Doppler and B-scan modes, wherein the improvement comprises, a dual transducer arrangement comprising first and second transducers associated with different operating mode systems of an ultrasonic imaging apparatus, said first and second transducers each comprising a generally semicylindrical piezoelectric body formed with generally parallel semicircular opposite end surfaces and a flat side face, electrodes disposed on the opposite end surfaces of the transducer bodies for connection to the different operating mode systems of the ultrasonic imaging apparatus, means for focusing said transducers, and means for relatively movably mounting said first and second transducers at opposite sides of a mid-plane extending between the transducers with the flat side faces of the transducers closely adjacent said mid-plane.

2. In an ultrasonic imaging apparatus as defined in claim 1 wherein said generally parallel semicircular end surfaces of the piezoelectric bodies are substantially flat, said focusing means including acoustic lenses at one said end surface of each of the transducer bodies.

3. In an ultrasonic imaging apparatus as defined in claim 1 wherein said focusing means includes means forming said piezoelectric bodies with curved generally parallel opposite end surfaces, one of which end surfaces is concave.

4. In an ultrasonic imaging apparatus as defined in claim 1 wherein said focusing means includes an electrode array disposed on at least one end surface of each of the piezoelectric bodies for use in electronic focusing thereof.

5. In an ultrasonic imaging apparatus as defined in claim 4 wherein said apparatus includes systems operating in the pulsed Doppler and pulsed B-scan modes, which systems each include a transmitter/receiver unit, said focusing means including electrical signal delay means connecting at least some of the electrodes of the electrode arrays to associated transmitter/receiver units.

6. In an ultrasonic imaging apparatus as defined in claim 1 wherein said transducers are focused at said mid-plane at substantially equal distances from said transducers.

7. In an ultrasonic imaging apparatus as defined in claim 1 wherein said mounting means includes means for mounting said first and second transducers for relative movement along generally parallel linear paths, and wherein said transducers are at least momentarily located with the flat side faces of the transducer bodies directly opposite and closely adjacent one another during relative movement of said transducers along said parallel paths.

8. In an ultrasonic imaging apparatus as defined in claim 1 wherein said first and second transducers are independently positionable along generally parallel linear paths extending generally normal to the respective transducer acoustic axes.

9. In an ultrasonic imaging apparatus as defined in claim 8 wherein said transducers are focused at said mid-plane at substantially equal distances from said transducers for focusing into a common region along the mid-plane.

10. First and second transducers for use with ultrasonic imaging appartus which functions in dual operating modes, said transducers comprising, first and second piezoelectric plates each of which is formed with generally semicircular parallel opposite end surfaces and flat and generally semicylindrical side edges, electrodes at the opposite end surfaces of the piezoelectric plates, and means for relatively movably mounting said first and second plates with said flat side edges of the plates at least momentarily positioned closely adjacent one another.

11. The first and second transducers as defined in claim 10 including, first and second focusing means associated with said respective first and second transducers for focusing the same at substantially equal distances from the transducers at a midplane between said transducers.

12. The first and second transducers as defined in claim 10 including, first and second acoustic lenses attached to said first and second transducers, respectively, for focusing the same.

13. The first and second transducers as defined in claim 10 wherein, said first and second plates are generally semi-bowl shaped for focusing the same.

14. The first and second transducers as defined in claim 10 wherein, said electrodes at at least one end surface of each of the piezoelectric plates comprise an electrode array for use in electronic focusing of the transducers.

15. The first and second transducers as defined in claim 14 wherein, said electrode arrays each include generally semiannular electrode members concentrically located on one end surface of the piezoelectric plates.

16. The first and second transducers as defined in claim 10 including, means for moving said first and second plates along linear generally parallel paths parallel to the flat side edges formed thereon.

17. The first and second transducers as defined in claim 10 including, means for independently positioning said first and second transducers along generally parallel linear paths extending generally normal to the respective transducer acoustic axes.

18. The first and second transducers as defined in claim 17 wherein said first and second transducers are focused at substantially equal distances from the transducers at a mid-plane between said transducers for focusing into a common region along the mid-plane.

* * * * *